(12) United States Patent
Castro (10) Patent No.: US 12,390,252 B2
(45) Date of Patent: Aug. 19, 2025

(54) FRACTURE REDUCTION DEVICE

(71) Applicant: FKNA, LLC, Louisville, KY (US)

(72) Inventor: Frank Castro, Louisville, KY (US)

(73) Assignee: MEDICAL PATENTS LLC, Nicholasville, KY (US)

( * ) Notice: Subject to any disclaimer, the term of this patent is extended or adjusted under 35 U.S.C. 154(b) by 174 days.

(21) Appl. No.: 18/034,183

(22) PCT Filed: Mar. 6, 2022

(86) PCT No.: PCT/US2022/019053
§ 371 (c)(1),
(2) Date: Apr. 27, 2023

(87) PCT Pub. No.: WO2022/225616
PCT Pub. Date: Oct. 27, 2022

(65) Prior Publication Data
US 2024/0016524 A1 Jan. 18, 2024

Related U.S. Application Data

(60) Provisional application No. 63/176,304, filed on Apr. 18, 2021.

(51) Int. Cl.
*A61B 17/72* (2006.01)
*A61B 17/00* (2006.01)
*A61B 90/00* (2016.01)

(52) U.S. Cl.
CPC ...... *A61B 17/7275* (2013.01); *A61B 17/7225* (2013.01); *A61B 2017/00539* (2013.01); *A61B 2017/00557* (2013.01); *A61B 2090/064* (2016.02)

(58) Field of Classification Search
CPC ............ A61B 17/7275; A61B 17/7225; A61B 2017/00539; A61B 2017/00557; A61B 2090/064
See application file for complete search history.

(56) References Cited

U.S. PATENT DOCUMENTS

| | | |
|---|---|---|
| 4,787,899 A | 11/1988 | Lazarus |
| 8,083,741 B2 | 12/2011 | Morgan et al. |
| 8,128,626 B2 | 3/2012 | Justin |
| 8,715,284 B2 | 5/2014 | Culber |
| 9,283,006 B2 | 3/2016 | Fonte |
| 2002/0032441 A1 | 3/2002 | Mische |
| 2008/0255559 A1 | 10/2008 | Leyden et al. |
| 2009/0143781 A1 | 6/2009 | Mische |
| 2009/0182336 A1 | 7/2009 | Brenzel et al. |
| 2011/0004255 A1 | 1/2011 | Weiner et al. |
| 2012/0065638 A1 | 3/2012 | Moore |
| 2012/0184999 A1 | 7/2012 | Khanna |
| 2013/0023875 A1 | 1/2013 | Harris et al. |
| 2013/0023876 A1 | 1/2013 | Rabiner et al. |
| 2013/0072933 A1 | 3/2013 | Biedermann et al. |
| 2013/0296861 A1 | 11/2013 | Tontz |
| 2015/0223849 A1 | 8/2015 | McCormick et al. |
| 2017/0290614 A1 | 10/2017 | Weiner et al. |

FOREIGN PATENT DOCUMENTS

WO WO2020076383 4/2020

*Primary Examiner* — Nicholas J Plionis
(74) *Attorney, Agent, or Firm* — BUSINESS PATENT LAW, PLLC (57) ABSTRACT

The present invention is a fracture reduction device or system adapted for use in bone cavities. The current device is particularly useful in surgical procedures involving fractured bones.

20 Claims, 5 Drawing Sheets

FRACTURE REDUCTION DEVICE

BACKGROUND OF THE INVENTION

A. Field of the Invention

Among other things, the present invention is a device or system that has interlocking first and second members. The current device is useful in the treatment of mammalian bone fractures.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references. References that may indicate a state-of-the-art for the current invention include: 1) US Published Patent Application 20020032444—Mische; 2) US Published Patent Application 20110004255—Weiner, et al.; 3) US Published Patent Application No. 20090143781—Mische; 4) U.S. Pat. No. 8,715,284—Culbert; 5) US Published Patent Application 20080255559—Leyden, et al.; 6) U.S. Pat. No. 8,128,626—Justin; 7) U.S. Pat. No. 9,283,006—Fonte; 8) US Published Patent Application 20120184999—Khanna; 9) US Published Patent Application 20120065638—Moore; 10) US Published Patent Application 20130072933—Bidermann, et al.; 11) US Published Patent Application 2013029686—Tonz; 12) US Published Patent Application 20150223849—McCormich, et al.; and 2017029061—Weiner, et al.

Among other things, none of the above listed references disclose a fracture reduction device (20) connecting two fractured segments (204, 206) across a fracture site (202) of a broken long bone (200); the fracture reduction device (20) comprising: a) a semi-rigid cylindrical male member (30), distinct from the two fractured segments (204, 206), comprising: i) a tip (35) at a first end (36); ii) first interlockers (50) circumscribing a portion of an outward side (44) of the semi-rigid first cylindrical body (32) of male member (30); iii) a first expandable balloon (60) comprising a first orifice (54); the expandable first balloon (60) positioned between the first interlockers (50) and the tip (34); and iv) a duct (40) extending from a second end (38) of the semi-rigid first cylindrical body (32) of male member (30); the duct (40), connected to or in connection with the first orifice (54), adapted for delivery of hydraulic fluid to expand the first expandable balloon (60), wherein prior to expansion, the first expandable balloon (60) is positioned inside a second medullary cavity section (208s), and subsequent to expansion of the first balloon (60), the duct (40) is clamped, crimped or plugged; b) a female member (70) receiving the male member (30) and distinct from the two fractured segments (204, 206); the female member (70) comprising: i) a second cylindrical body (72) comprising: a first open end (74), a second open end (76), a channel (80) and a channel wall (82); ii) second complimentary interlockers (84) positioned on an inward side (83) of the channel wall (82) and an oblique slit (86) extending through outward (81) and inward sides (83) of the channel wall (82); iii) a second expandable balloon (90) comprising a second orifice (92); the second expandable balloon (90) positioned between the second open end (76) and the second complimentary interlockers (84); and iii) a conduit (96) extending longitudinally from a second opening (78) of the second open end (76) to the channel (80) and connected to or in communication with the second orifice (92), adapted for delivery of hydraulic fluid to expand the second expandable balloon (90), wherein prior to expansion, the second balloon (90) is positioned inside a first medullary cavity section (208f), and subsequent to expansion of the second balloon (90), the conduit (96) is clamped, crimped or plugged; and c) one or more sensors (100) positioned about first interlockers (50) and second lockers (84); the sensors (100) adapted to transmit sensed data to a computing device for calculation of tension applied to the first and second medullary cavities (208f, 208s).

Among other things, none of the above listed references disclose a fracture reduction device (20) connecting two fractured segments (204, 206) across a fracture site (202) of a broken bone (200); the fracture reduction device (20) comprising: a) a cylindrical male member (30) comprising: i) first interlockers (50) circumscribing a portion of an outward side (44) of the cylindrical male member (30); ii) a first expandable balloon (60) adapted for positioning inside a second medullary cavity section (208s); the first expandable balloon (60) comprising a first orifice (54); and iii) a duct (40) positioned on an inward side (45) of the cylindrical male member (30); the duct (40) connected to or in connection with the first orifice (54) and adapted for delivery of hydraulic fluid to expand the first expandable balloon (60); and b) a female member (70) comprising: i) a cylindrical body (72) comprising a first end (74), a second end (76), a channel (80) surrounded by a channel wall (82), an oblique slit (86) extending through the outward (81) and inward sides (83) of the channel wall (82) and second complimentary interlockers (84), positioned on the inward side (83) of the channel wall (82), receiving the first interlockers (50); ii) a second expandable balloon (90) adapted for positioning inside a first medullary cavity section (208f), wherein the second expandable balloon (90) comprises a second orifice (92); and iii) a conduit (96) connected to or in communication with the second orifice (92) and adapted for delivery of hydraulic fluid to expand the second expandable balloon (90).

Among other things, none of the above listed references disclose a fracture reduction device (20) connecting two fractured segments (208f, 208s) across a fracture site (202) of a broken bone (200); the fracture reduction device (20) comprising: a) a cylindrical male member (30) adapted to penetrate a second fractured segment (208s); the cylindrical male member (30) comprising: i) first interlockers (50) positioned on a portion of an outward side (44) of the cylindrical male member (30); ii) a first expandable balloon (60) adapted to contact an inward portion of the second fractured segment (208s); and iii) a duct (40) positioned on an inward side (45) of the male cylindrical member (30); the duct (40) adapted to supply fluid to the first expandable balloon (60); and b) a female receptacle (70) configured to receive a portion of the cylindrical male member (30); the female member (70) comprising: i) a first end (74), a second end (76), a channel (80) surrounded by a channel wall (82), a slit (86) in the channel wall (82) and second complimentary interlockers (84) positioned on an inward side (83) of the channel wall (82) interlocking with the first interlockers (50); ii) a second expandable balloon (90) adapted to contact an inward portion of the first fractured segment (208f); and iii) a conduit (40), positioned inward from the channel wall (82), adapted to supply fluid to the second expandable balloon (90).

Prior to the current invention, in minimally first line surgeries to repair a fractured long bone, surgeons would pass a guide wire through the proximal fractured side into the distal fractured side. Generally, a rod was also passed over the guide wire. Through the use of forces external to the outward surfaces of opposed fractured sides, the fractured sides were manipulated into positions that approximated their pre-fracture state. In the proximal and distal fractured sides, the rod was locked into place with screws. Locking the rod minimized the vertical, horizontal and rotational movement of the implant, and in many cases, such stabilization of the injured environment was sufficient for bone healing. However, there are many times when the first line prior art surgical methods failed to adequately anatomically realign the fractured sections and subsequent surgery was required to improve healing of the fractured bone. By way of illustration, due to resorption of bone or gaps caused bone loss from the injury, prior art first line surgeries were frequently inadequate to improve healing of the fracture.

SUMMARY OF THE INVENTION

The present invention provides a biocompatible implant or system that can be inserted into opposed cavities of fractured sides of bone. The current device or implant can be provided with male and female components that have interlocking teeth to limit movements of the female and male components. Among other things, the male device is provided with a body, a duct and a balloon and the female component is provided with a body, a channel and a balloon. Both the female and male members are provided with interlockers.

After implantation into a medullary cavity of a fractured long bone, the balloons can be expanded to contact a healthy (unbroken) area of the wall surrounding the medullary cavity. Among other things, the implant's expanded balloons hold the opposed sides of fractured bone and allow the opposed sides to be compressed against each other and to assist with the healing of the fracture.

It has been estimated that between five to ten percent of long bone fractures treated with prior art surgical implants, techniques and procedures fail to heal. Such postoperative conditions as bone resorption, improper alignment of the opposed sides of the fractured bone or low grade infection can precipitate a non-union of fracture fragments. When the long bone fracture fails to heal after utilizing prior art fixation systems, a second or third surgical procedure may be required to create a union between the fractured fragments. For example, when intramedullary rod fixation was used in the first surgical treatment, the implanted rod holds the fracture fragments and bone length constant by placing screws at opposite ends of the rod. Stabilizing the repaired bone's fractured sides to a constant length reduces the dynamic compression between the fractured sides. It is believed that dynamic compression enhances healing between the fractured sides of the broken bone.

When using the prior art's intramedullary rods, if postoperative non-union occurred, a first treatment option was to remove the distal screws to allow for dynamic compression or a second treatment option required a second surgery to remove the first implant rod and replace the first rod with a second larger rod. The second surgery's implantation of the second larger rod was typically more invasive than the first surgical procedure.

From the initial surgical procedure to repair the broken bone, use of the current invention allows for dynamic compression of the opposed broken sides of the fractured bone. It is believed that the dynamic compression provided by the present invention's system of interlockers reduces the risk of a second or third surgical procedure.

An aspect of the present invention is to provide a fracture reduction device connecting two fractured segments across a fracture site of a broken long bone; the fracture reduction device comprising: a) a semi-rigid cylindrical male member, distinct from the two fractured segments, comprising: i) a tip at a first end; ii) first interlockers circumscribing a portion of an outward side of the semi-rigid cylindrical male member; iii) a first expandable balloon comprising a first orifice; the expandable balloon positioned between the first interlockers and the tip; and iv) a duct extending from a second end of the semi-rigid cylindrical male member; the duct, connected to or in connection with the first orifice, adapted for delivery of hydraulic fluid to expand the first expandable balloon, wherein prior to expansion the first balloon is positioned inside a second medullary cavity section, and subsequent to expansion of the first balloon, the duct is clamped, crimped or plugged; b) a female member receiving the male member and distinct from the two fractured segments; the female member, comprising: i) a cylindrical body comprising: a first open end, a second open end, a channel and a channel wall; second complimentary interlockers positioned on an inward side of the channel wall and an oblique slit extending through outward and inward sides of the channel wall; ii) a second expandable balloon comprising a second orifice; the second expandable balloon positioned between the second open end and the second complimentary interlockers; and iii) a conduit extending longitudinally from a second opening of the second open end to the channel and connected to or in communication with the second orifice, adapted for delivery of hydraulic fluid to expand the second expandable balloon, wherein prior to expansion the second balloon is positioned inside a first medullary cavity section, and subsequent to expansion of the second balloon, the conduit is clamped, crimped or plugged; and c) one or more sensors positioned about first interlockers and second lockers; the sensors adapted to transmit sensed data to a computing device for calculation of tension applied to the first and second medullary cavities.

Still another aspect of the present invention is to provide a fracture reduction device connecting two fractured segments across a fracture site of a broken bone; the fracture reduction device comprising: a) a cylindrical male member comprising: i) first interlockers circumscribing a portion of an outward side of the cylindrical male member; ii) a first expandable balloon adapted for positioning inside a second medullary cavity section; the first expandable balloon comprising a first orifice; and iii) a duct positioned on an inward side of the cylindrical male member; the duct connected to or in connection with the first orifice and adapted for delivery of hydraulic fluid to expand the first expandable balloon; and b) a female member comprising: i) a cylindrical body comprising a first end, a second end, a channel surrounded by a channel wall, an oblique slit extending through the outward and inward sides of the channel wall and second complimentary interlockers, positioned on an inward side of the channel wall, receiving the first interlockers; ii) a second expandable balloon adapted for positioning inside a first medullary cavity section, wherein the second expandable balloon comprises a second orifice; and iii) a conduit connected to or in communication with the second orifice and adapted for delivery of hydraulic fluid to expand the second expandable balloon.

It is still another aspect of the present invention to provide a fracture reduction device connecting two fractured segments across a fracture site of a broken bone; the fracture reduction device comprising: a) a cylindrical male member adapted to penetrate a second fractured segment; the cylindrical male member comprising: i) first interlockers positioned on a portion of an outward side of the cylindrical male member; ii) a first expandable balloon adapted to contact an inward portion of the second fractured segment; and iii) a duct positioned on an inward side of the male cylindrical member; the duct adapted to supply fluid to the first expandable balloon; and b) a female receptacle configured to receive a portion of the cylindrical male member; the female member comprising: i) a first end, a second end, a channel surrounded by a channel wall, a slit in the channel wall and second complimentary interlockers positioned on an inward side of the channel wall interlocking with the first interlockers; ii) a second expandable balloon adapted to contact an inward portion of the first fractured segment; and iii) a conduit, positioned inward from the channel wall, adapted to supply fluid to the second expandable balloon.

It is the novel and unique interaction of these simple elements which creates the apparatus and methods, within the ambit of the present invention. Pursuant to Title 35 of the United States Code, descriptions of preferred embodiments follow. However, it is to be understood that the best mode descriptions do not limit the scope of the present invention.

DESCRIPTION OF THE PREFERRED EMBODIMENTS

Although the disclosure hereof is detailed to enable those skilled in the art to practice the invention, the embodiments published herein merely exemplify the present invention.

In the most general sense, the present invention is a biocompatible system, device or implant adapted for insertion into opposed cavities of first and second sides of a fractured bone. For some preferred embodiments of the current invention, after implantation, some portions of the implant contact the cortex of healthy (uninjured) bone. The current invention can be particularly useful for the treatment of fractured mammalian long bones.

In the practice of the current system, a guide wire is introduced to the fracture site. Thereafter, the system's implant or combination is introduced to the fracture site and the guidewire removed. A first balloon is placed inside a first side of fractured bone and a second balloon is placed inside a second side of fractured bone. The female member is provided with a slit allowing the female member to be wrapped around the male member when the male and female member are positioned inside the medullary cavity.

Unlike prior surgical methods that use forces external to the first outward side and second outward side of the fractured bone to align the first and second sides of the fractured bone, the current implant allows the combination of the interlocked male and female members to apply internal forces to the inner cavities of the first and second fractured sides to realign the first and second fractured sides. In a preferred practice of the current fracture reduction device, it is anticipated that the surgeon will align the distal side by expanding the distal device's expandable balloon applying force to the distal side's medullary to pull and align the distal side with the proximal side of the fracture. When adequate reduction has occurred, the surgeon can expand the balloon of the female member to engage the medullary cavity and utilize the interlockers to adjust compressive forces applied to the fracture site. During surgery, the current implant can be used to align the first and second sides of the fractured bone and subsequent to surgery the implanted combination allows for dynamic compression of the aligned and proximal first and second sides of the fractured bone.

Among other things, the current system or implant includes interlocking male and female members or components. The male member is provided with a duct, balloon and interlocker and the female member is provided with a slit, channel, balloon and complementary interlocker. For select preferred embodiments of the current fracture reduction device, guide wires can be utilized to assist placement of the fracture reduction device into the fractured sections of bone.

Anatomic realignment of opposed sides of the fracture is currently understood to promote healing of the fracture, and it is believed that the closeness and precision that can be provided by the current device's anatomic realignment of the first and second sides of the fracture further improves healing of the fracture. The present invention's expandable balloons are compatible with bone cavities of differing diameters and along with the system disclosed in Applicant's pending "Long Bone Fracture Reduction System" Application, it is believed that no prior surgical devices and methods can provide better control of postoperative horizontal, lateral and rotational movements of the compressed first and second sides of fractured bone.

In select preferred embodiments of the invention, the channel and duct can create a continuous passage extending along a common longitudinal axis of the fracture reduction device. The system's passage can transport: tissue away from the injury and or irrigation to and away from the injury. The fracture reduction device's passage can also be used to transport biocompatible devices/substances, such as adhesives, cameras, cannulas, catheter, fiber optics, implants other than the current invention, osteogenics, pharmaceuticals, etc.

Along with stabilizing fractures, the current invention can be adapted for use to prophylactically treat weakened but unbroken bones, e.g., cancer, osteoporosis and non-unions platelets. After implantation, the present combination can also be used to transport adhesives, biopsies, chemotherapy, iliac crest marrow, parathyroid hormone, etc.

Preferred embodiments of the present invention are manufactured of titanium alloys, stainless steel, non-resorbable polymers or any other composition acceptable in the art. Within the scope of the present invention, it has advantageously been discovered that female body can have a length of from about one centimeter to about fifty centimeters and a diameter of from about two millimeters to about twenty millimeters. The male body can have a length of from about one centimeter to about fifty centimeters and a diameter of from about two millimeters to about twenty millimeters. Meshes of the current invention can have a length of from about one-half centimeter to about twenty-five centimeters and can be expanded from about two and one-half millimeters to about three centimeters. Tips of the current combination can have a diameter of from about one and one-half millimeter to about ten millimeters and a length of from about three millimeters to about twenty millimeters.

Figure 1:
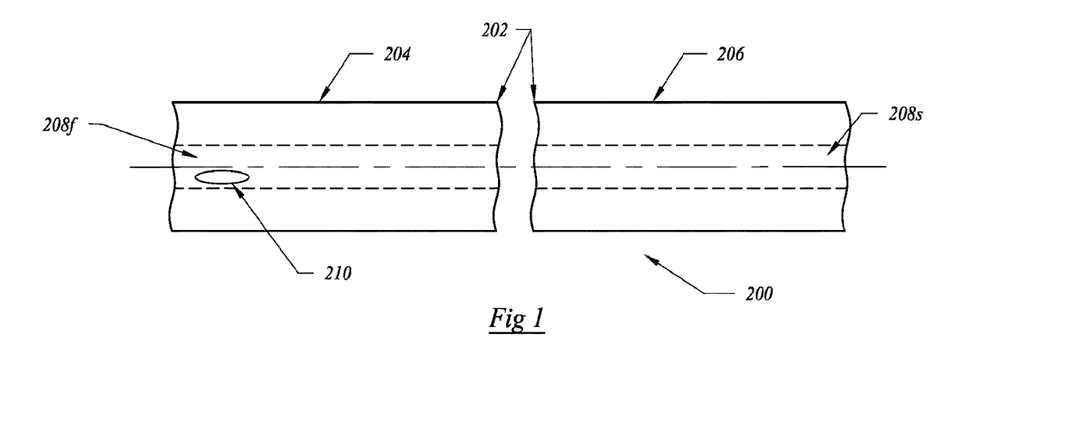
FIG. 1 is a perspective of a fractured bone (200) and fracture site (202).

FIG. 1 is a perspective of a fractured bone (200) and fracture site (202). First fracture section (204) includes first medullary cavity section (208f) and second fracture section (206) includes second medullary cavity section (208s). When first fracture section (204) and second fracture section (206) are rejoined, medullary cavity (208) can be reestablished by the connection between first medullary cavity section (208f) and second medullary cavity section (208s). For select preferred embodiments of the current invention, first fracture section (204) is provided with surgical incision (210).

Figure 2:
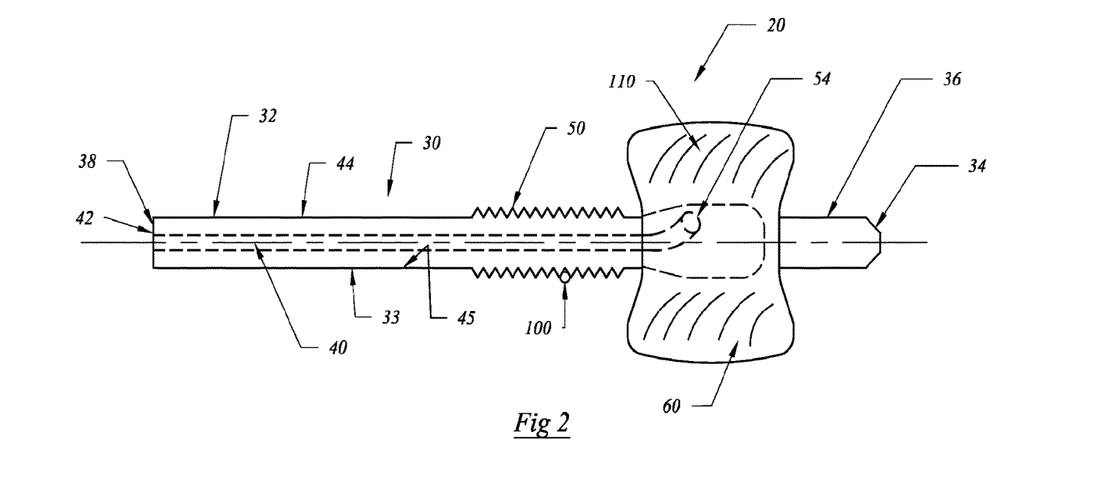
FIG. 2 is a perspective of a preferred embodiment of male member (30) of fracture reduction device (20).

FIG. 2 is a perspective of a preferred embodiment of male member (30) of fracture reduction device (20). Select preferred embodiments of male member (30) can be semi-rigid. As shown in FIG. 2, balloon (60) is expanded. In operation of the current fracture reduction device (20), balloon (60) is not expanded until closed tip (34), first end (36) and balloon (60) are positioned within second medullary cavity section (208s).

Select preferred embodiments of male member (30) are provided with first cylindrical body (32) and closed tip (34) opposite second end (38) of male member (30). First interlockers (50) circumscribe a portion of outward side (44) of cylindrical body (32) of male member (30). Duct (40) extends from opening (42) of second end (38) of male member (30) to first balloon (60) and is provided with first orifice (54) for delivery of hydraulic fluid to expand first balloon (60). In select preferred embodiments, duct (40) is positioned on inward side (45) of cylindrical body (32) of male member (30). A hydraulic pump (not shown) can be utilized to supply fluid to duct (40). Subsequent to expansion of first balloon (60), duct (40) can be clamped, crimped or plugged to assist with maintaining the appropriate medical expansion of first balloon (60) contacting second medullary cavity section (208s).

Figure 3:
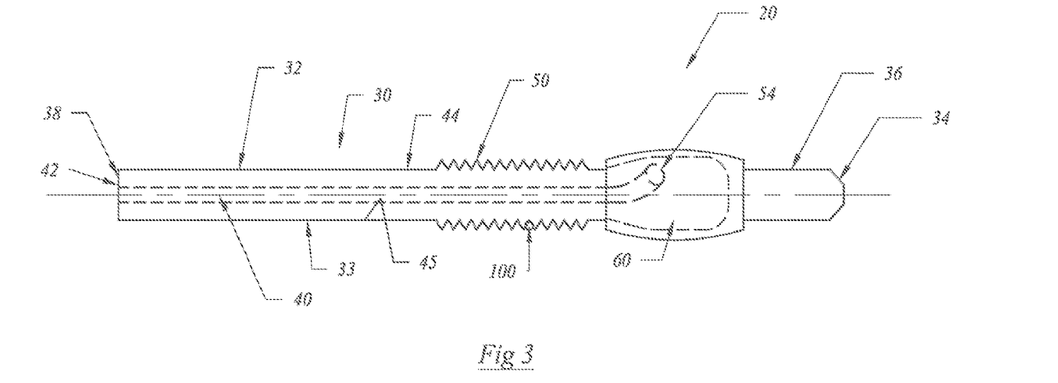
FIG. 3 enables a male member (30) of fracture reduction device (20) identical to male member (30) of FIG. 1, except that balloon (60) is unexpanded.

FIG. 3 enables a male member (30) of fracture reduction device (20) identical to male member (30) of FIG. 1, except that balloon (60) is unexpanded.

Figure 4:
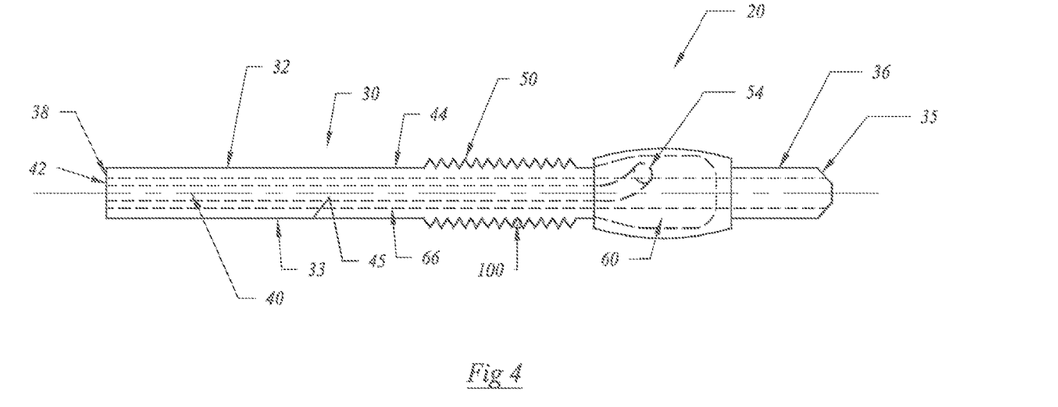
FIG. 4 is a perspective of similar male member (30) of fracture reduction device (20).

FIG. 4 is a perspective of similar male member (30) of fracture reduction device (20). In this preferred embodiment, expandable balloon (60) is unexpanded and male member (30) is provided with passage (66) extending from opening (42) of second end (38) of male member (30) through open tip (35). In operation of the current fracture reduction device (20), balloon (60) is not expanded until open tip (35), first end (36), balloon (60) and a majority of or all of first interlockers (50) are positioned within second medullary cavity section (208s). First interlockers (50) circumscribe a portion of outward side (44) of cylindrical body (32) of male member (30). Duct (40) extends from opening (42) of second end (38) of male member (30) to balloon (60) and is provided with first orifice (54) for delivery of fluid to expandable balloon (60). A hydraulic or other pump (not shown) can be utilized to supply fluid to duct (40). Subsequent to expansion of balloon (50), duct (40) can be clamped, crimped or plugged to assist with maintaining the appropriate medical expansion of balloon (60).

Figure 5:
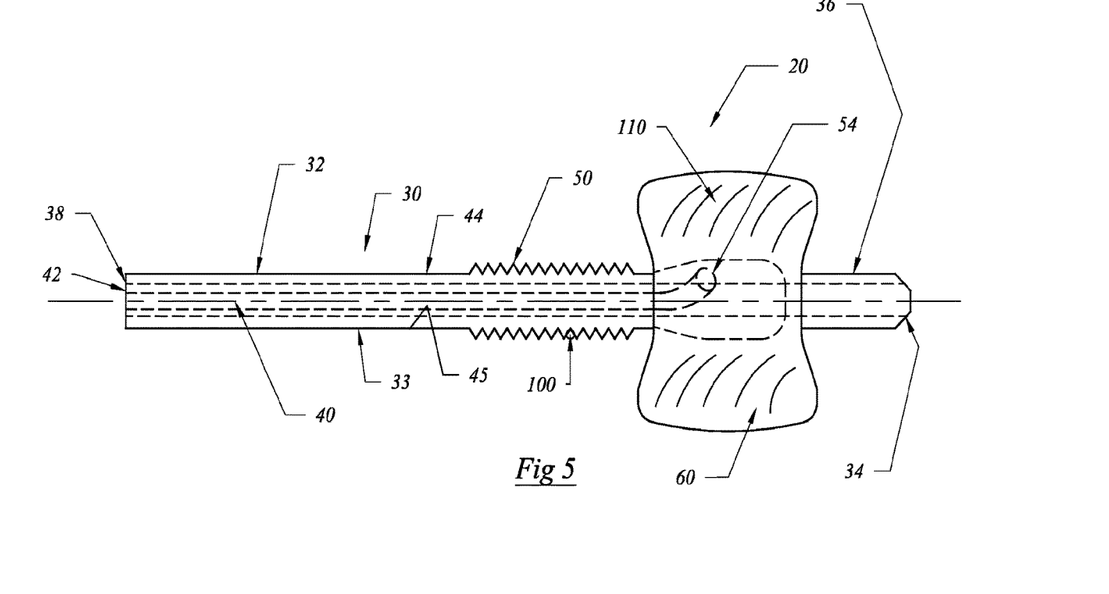
FIG. 5 enables a male member (30) of fracture reduction device (20) identical to male member (30) of FIG. 4, except that balloon (30) is expanded.

FIG. 5 enables a male member (30) of fracture reduction device (20) identical to male member (30) of FIG. 4, except that balloon (30) is expanded.

Figure 6:
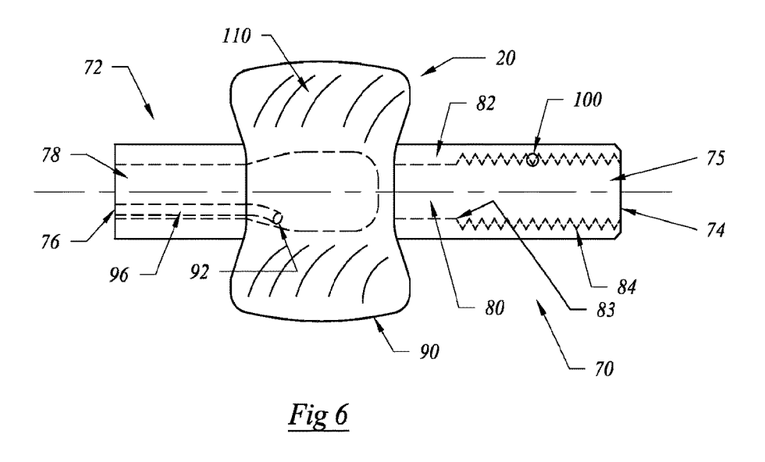
FIG. 6 is a lateral perspective of female member (70) of fracture reduction device (20) where balloon (90) is expanded.

FIG. 6 is a lateral perspective of female member (70) of fracture reduction device (20) where balloon (90) is expanded. For select preferred embodiments, female member (70) can be bendable. In use, female member (70) fits about the cylindrical body (32) of male member (30). Second complimentary interlockers (84) are positioned on inward side (83) of channel wall (82) of channel (80) and adapted to engage and interlock with interlockers (50) of male member (30). Balloon (90) is generally not expanded until interlockers (84) of female member (70) and interlockers (50) of male member are engaged.

Female member (70) is provided with second cylindrical body (72), first open end (74) and second open end (76). Channel (80) extends longitudinally from second opening (78) of second open end (76) to first opening (75) of first open end (74). Second orifice (92) connects or is connected to balloon (90) and conduit (96) adapted to supply fluid to balloon (90). A hydraulic or other pump (not shown) can be utilized to supply fluid to conduit (96). Subsequent to expansion of balloon (90), conduit (96) can be clamped, crimped or plugged to assist with maintaining the appropriate medical expansion of balloon (90) contacting first medullary cavity section (208f). Second balloon (90) is adapted to expand radially from female member (70) and engage first medullary cavity section (208f).

In use, first interlockers (50) and complimentary second interlockers (84) engage and interlock with each other. When fracture reduction device (20) engages first medullary cavity section (208f) and second medullary cavity section (208s), second expandable balloon (90) is remote from tip (34 or 35) of male member (30) and interlockers (50, 84) are positioned between the balloons (60, 90).

Figure 7:
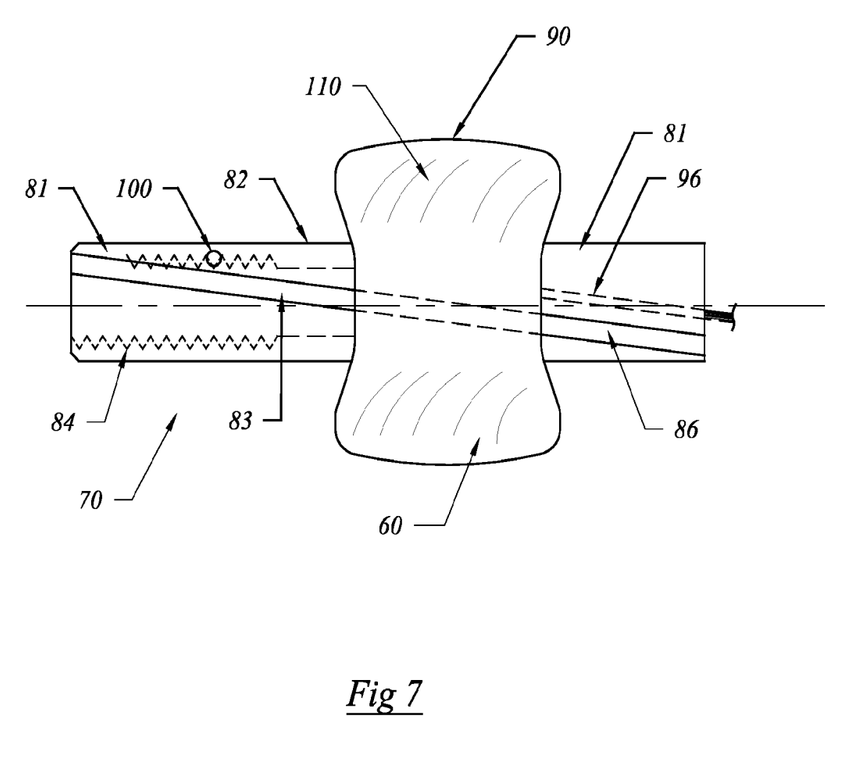
FIG. 7 is a lateral perspective of female member (70) of fracture reduction device (20) provided with an oblique slit (86).

As shown in FIG. 7, select preferred embodiments of female member (70) of fracture reduction device (20) are provided with an oblique slit (86) extending from outward side (81) of channel wall (82) and through inward side (83) of channel wall (82). Oblique slit (86) allows fitting of female member (70) about male member (30).

Select preferred embodiments of male member (30) and female member (70) can be provided with sensors (100). One or more sensors (100) can be positioned about first interlockers (50) and second complimentary interlockers (84) to sense interlocking pressures associated with first interlockers (50) and second interlockers (84). By way of illustration, sensors (100) can transmit sensed data to a computing device remote from fracture reduction device (20) for calculation of tension applied to first fracture section (204) and second fracture section (206).

As shown in FIGS. 2 and 5-7, balloons (60, 90) can be provided with surface treatments (110) adapted to improve frictional forces between balloons (60, 90) and cavity walls of first medullary cavity section (208f) and second medullary cavity section (208s).

On engagement of interlockers (50) and complimentary interlockers (84), resistive surfaces of interlockers (50) and second complimentary interlockers (84) allow for the application of constant or increasing compressive force between male member (30) and female member (70). In other words, the resistive surfaces allow movement or adjustment of male member (30) and female member (70) to increase tension applied to first fracture section (204) and second fracture section (206).

In operation of the fracture reduction device (20), male member (30) is inserted through surgical incision (210) into first medullary cavity section (208f) and advanced into second medullary cavity section (208s). Where the bone is fractured in multiple locations creating multiple medullary cavity sections, regardless of the number of medullary cavity sections, second medullary cavity section (208s) is the medullary cavity section distal from first cavity section (208f). After male member is positioned in second medullary cavity section (208s), balloon (60) can be expanded to engage wall of second medullary cavity section (208s).

After male member (30) is positioned in second medullary cavity section (208s), female member (70) is inserted through surgical incision (210) into first medullary cavity section (208f) and advanced such that interlockers (84) engage interlockers (50) of male member (30). Subsequent to engagement of interlockers (84) and interlockers (50), balloon (90) of female member (70) can be expanded to engage wall of second medullary cavity section (208s). After expansion of balloons (60, 90), interaction between complimentary interlockers (84) and interlockers (50) is utilized to adjust alignment of first medullary cavity section (208f) and second medullary cavity section (208s) and any medullary cavity section therebetween. Interaction between interlockers (84) and interlockers (50) is also used to establish tension applied to first medullary cavity section (208f) and second medullary cavity section (208s) and any medullary cavity section therebetween. Use of the current fraction reduction device (20) can reduce fracture site (202), realign and reconnect first medullary cavity section (208f) and second medullary cavity section (208s) and any medullary cavity of bone (200).

Figure 8:
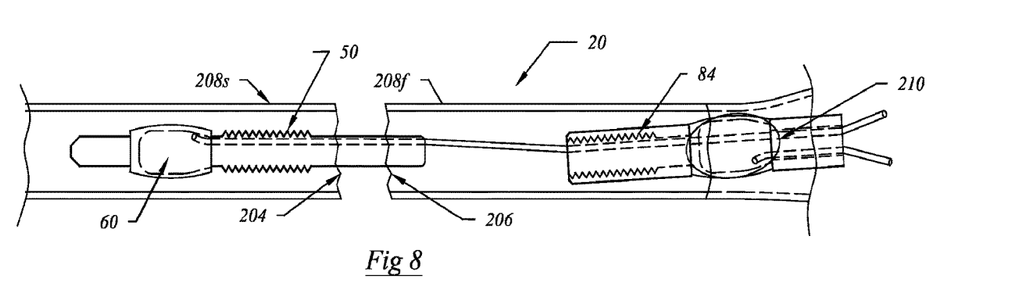
FIGS. 8-10 exemplify uses of the fracture reduction device.
Figure 9:
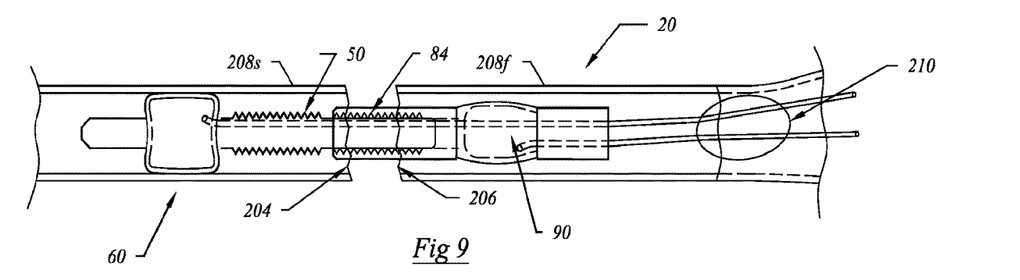
Figure 10:
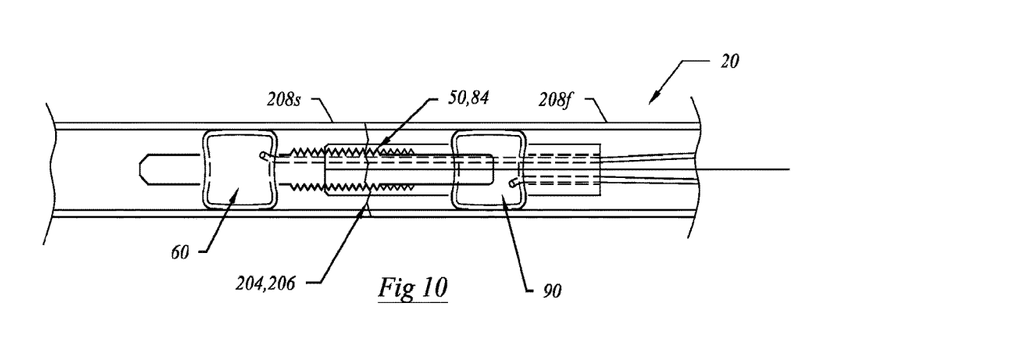

FIGS. 8-10 show uses of the current fracture reduction device (20).

FIG. 8 portrays the fracture reduction device (20) inserted through incision (210) into first and second medullary cavity sections (208f, 208s) where first fracture section (204) and second fracture section (206) are not rejoined; the interlockers (50, 84) are not interlocked and balloons (60, 90) are unexpanded.

FIG. 9 portrays the fracture reduction device (20) inserted through incision (210) into first and second medullary cavity sections (208f, 208s) where first fracture section (204) and second fracture section (206) are not rejoined but closer in proximity than shown in FIG. 8; the interlockers (50, 84) have initial contact and balloon (60) is expanded and balloon (90) is unexpanded.

FIG. 10 portrays the fracture reduction device (20) inserted through incision (210) into first and second medullary cavity sections (208f, 208s) where first fracture section (204) and second fracture section (206) are rejoined; the interlockers (50, 84) have substantial contact and balloons (60, 90) are expanded and fracture reduction device (20) is supplying tension to first and second medullary cavity sections (208f, 208s).

Applicant has enabled, described and disclosed the invention as required by Title 35 of the United States Code and the Articles of the Patent Cooperation Treaty.

What is claimed is:

1. A fracture reduction device (20) configured to connect two fractured segments (204, 206) across a fracture site (202) of a broken long bone (200); the fracture reduction device (20) comprising:
   a) a semi-rigid cylindrical male member (30), distinct from the two fractured segments (204, 206), comprising:
      i) a tip (34) at a first end (36);
      ii) first interlockers (50) circumscribing a portion of an outward side (44) of a semi-rigid first cylindrical body (32) of male member (30);
      iii) a first expandable balloon (60) comprising a first orifice (54); the first expandable balloon (60) positioned between the first interlockers (50) and the tip (34); and
      iv) a duct (40) extending from a second end (38) of the semi-rigid first cylindrical body (32) of male member (30); the duct (40), connected to or in connection with the first orifice (54), adapted for delivery of hydraulic fluid to expand the first expandable balloon (60), wherein prior to expansion, the first expandable balloon (60) is positioned inside a second medullary cavity section (208s), and subsequent to expansion of the first balloon (60), the duct (40) is clamped, crimped or plugged;
   b) a female member (70) receiving the male member (30) and distinct from the two fractured segments (204, 206); the female member (70) comprising:
      i) a second cylindrical body (72) comprising:
         a first open end (74), a second open end (76), a channel (80) and a channel wall (82);
      ii) second complimentary interlockers (84) positioned on an inward side (83) of the channel wall (82) and an oblique slit (86) extending through outward (81) and inward sides (83) of the channel wall (82);
      iii) a second expandable balloon (90) comprising a second orifice (92); the second expandable balloon (90) positioned between the second open end (76) and the second complimentary interlockers (84); and
      iii) a conduit (96) extending longitudinally from a second opening (78) of the second open end (76) to the channel (80) and connected to or in communication with the second orifice (92), adapted for delivery of hydraulic fluid to expand the second expandable balloon (90), wherein prior to expansion, the second balloon (90) is positioned inside a first medullary cavity section (208f), and subsequent to expansion of the second balloon (90), the conduit (96) is clamped, crimped or plugged; and
   c) one or more sensors (100) positioned about first interlockers (50) and second lockers (84); the sensors (100) adapted to transmit sensed data to a computing device for calculation of tension applied to the first and second medullary cavities (208f, 208s).

2. The fracture reduction (20) device of claim 1, wherein outer surfaces of the first and second balloons (60, 90) are provided with surface treatments (110) adapted to enhance frictional forces between the balloons (60, 90) and the first and second medullary cavities (208f, 208s).

3. The fracture reduction device (20) of claim 2, wherein the oblique slit (86) extends through the length of the female member (70).

4. The fracture reduction device (20) of claim 3, wherein the tip (34) is closed.

5. The fracture reduction device (20) of claim 3, wherein the male member (30) comprises a passage (66) extending from an opening (42) of the second end (38) of male (38) member through the tip (34) of male member (30)).

6. A fracture reduction device (20) configured to connect two fractured segments (204, 206) across a fracture site (202) of a broken bone (200); the fracture reduction device (20) comprising:
   a) a cylindrical male member (30) comprising:

i) first interlockers (50) circumscribing a portion of an outward side (44) of the cylindrical male member (30);

ii) a first expandable balloon (60) adapted for positioning inside a second medullary cavity section (208s); the first expandable balloon (60) comprising a first orifice (54); and iii) a duct (40) positioned on an inward side (45) of the cylindrical male member (30); the duct (40) connected to or in connection with the first orifice (54) and adapted for delivery of hydraulic fluid to expand the first expandable balloon (60); and b) a female member (70) comprising:

i) a cylindrical body (72) comprising a first end (74), a second end (76), a channel (80) surrounded by a channel wall (82), an oblique slit (86) extending through outward (81) and inward (83) sides of the channel wall (82) and second complimentary interlockers (84), positioned on the inward side (83) of the channel wall (82), receiving the first interlockers (50);

ii) a second expandable balloon (90) adapted for positioning inside a first medullary cavity section (208f), wherein the second expandable balloon (90) comprises a second orifice (92); and iii) a conduit (96) connected to or in communication with the second orifice (92) and adapted for delivery of hydraulic fluid to expand the second expandable balloon (90).

7. The fracture reduction device (20) of claim 6, wherein the first balloon (60) is expanded after positioning inside the second medullary cavity section (208s) and the second balloon (90) is expanded after positioning inside the first medullary cavity section (208f).

8. The fracture reduction device (20) of claim 6, wherein outer surfaces of the first and second balloons (60, 90) are provided with surface treatments (110) adapted to enhance frictional forces between the balloons (60, 90) and the first and second medullary cavities (208f, 208s).

9. The fracture reduction device (20) of claim 8, wherein the oblique slit (86) extends through the length of the female member (70).

10. The fracture reduction device (20) of claim 9 comprising one or more sensors (100) adapted to transmit sensed data to a computing device for calculation of tension applied to the first and second medullary cavities (208f, 208s).

11. The fracture reduction device (20) of claim 10, wherein a tip (34) of the male member (30) is closed.

12. The fracture reduction device (20) of claim 10, wherein an internal passage (66) extending a length of the cylindrical male member (30) is created by the inward side (45) of the cylindrical male member (30).

13. A fracture reduction device (20) configured to connect two fractured segments (208f, 208s) across a fracture site (202) of a broken bone (200); the fracture reduction device (20) comprising:

a) a cylindrical male member (30) adapted to penetrate a second fractured segment (208s); the cylindrical male member (30) comprising:

i) first interlockers (50) positioned on a portion of an outward side (44) of the cylindrical male member (30);

ii) a first expandable balloon (60) adapted to contact an inward portion of the second fractured segment (208s); and iii) a duct (40) positioned on an inward side (45) of the male cylindrical member (30); the duct (40) adapted to supply fluid to the first expandable balloon (60); and b) a female receptacle (70) configured to receive a portion of the cylindrical male member (30); the female member (70) comprising:

i) a first end (74), a second end (76), a channel (80) surrounded by a channel wall (82), a slit (86) in the channel wall (82) and second complimentary interlockers (84) positioned on an inward side (83) of the channel wall (82) interlocking with the first interlockers (50);

ii) a second expandable balloon (90) adapted to contact an inward portion of the first fractured segment (208f); and iii) a conduit (40), positioned inward from the channel wall (82), adapted to supply fluid to the second expandable balloon (90).

14. The fracture reduction device (20) of claim 13, wherein at least one of outer surfaces of the first or second balloons (60, 90) is provided with surface treatments (110).

15. The fracture reduction device (20) of claim 14 comprising one or more sensors (100) adapted to transmit sensed data to a computing device for calculation of tension applied to the first and second fracture segments (208f, 208s).

16. The fracture reduction device (20) of claim 15, wherein the first expandable balloon (60) comprises a first orifice (54) connected to the duct (40) and the second expandable balloon (90) comprises a second orifice (92) connected to the conduit (96).

17. The fracture reduction device (20) of claim 15, wherein the slit (86) is oblique and extends the length of the female member (70).

18. The fracture reduction device (20) of claim 17, wherein the first balloon (60) is expanded after positioning inside the second fractured section (208s) and the second balloon (90) is expanded after positioning inside the first fractured section (208f).

19. The fracture reduction device (20) of claim 17, wherein a tip (34) of the cylindrical male member (30) is closed.

20. The fracture reduction device (20) of claim 17, wherein an internal passage (66) extending a length of the cylindrical male member (30) is created by the inward side (45) of the cylindrical male member (30).

* * * * *